US012758428B2

(12) United States Patent
Dukovich

(10) Patent No.: US 12,758,428 B2
(45) Date of Patent: Oct. 13, 2026

(54) EAR HYGIENIC IMPLEMENTS AND KIT

(71) Applicant: Sunny Dukovich, Los Angeles, CA (US)

(72) Inventor: Sunny Dukovich, Los Angeles, CA (US)

( * ) Notice: Subject to any disclaimer, the term of this patent is extended or adjusted under 35 U.S.C. 154(b) by 330 days.

(21) Appl. No.: 18/399,459

(22) Filed: Dec. 28, 2023

(65) Prior Publication Data

US 2024/0216178 A1 Jul. 4, 2024

Related U.S. Application Data

(63) Continuation-in-part of application No. 16/859,642, filed on Apr. 27, 2020, now abandoned.

(51) Int. Cl.
*A61F 11/00* (2022.01)

(52) U.S. Cl.
CPC .................................. *A61F 11/006* (2013.01)

(58) Field of Classification Search
CPC ...... A61F 11/006; A61F 13/38; A61F 13/505; A45D 34/042; A45D 40/00; A45D 44/00; A45D 2200/1018; A46B 5/0095; A46B 2200/10; A54D 2200/1036; A61B 2017/320004; A61B 17/54; A61B 17/545; A61B 2017/00761; A61B 2017/00747
See application file for complete search history.

(56) References Cited

U.S. PATENT DOCUMENTS 4,748,990 A * 6/1988 Brown ................. A45D 34/042 401/277
2004/0097997 A1* 5/2004 Di Cecco ............ A61M 3/0262 606/162
2015/0225165 A1* 8/2015 Bloc .................... B65D 83/763 222/344

* cited by examiner

*Primary Examiner* — Kathleen S Holwerda
*Assistant Examiner* — James R Mcginnity
(74) *Attorney, Agent, or Firm* — James A. Italia; Italia IP

(57) ABSTRACT

An implement for cleaning ears is shown and described. The implement may include an elongated handle and assembly designed to connect with the elongated handle that serves as a cleaning head. The assembly may have a plastic cone, rubber overmold designed to fit over the plastic cone, and sponge designed to fit over the rubber overmold. The plastic cone can attach to the elongated handle by way of a screw-on threaded connection, prongs that mate with slits on the plastic cone, or a combination of these. The implement may be part of a kit also including a container of containing oil foam having oil, soap, and water; a package containing a supply of liquid permeable pads impregnated with anti-bacterial liquid; and a spray container containing antibacterial liquid. Optionally, the kit also includes a container containing a supply of liquid permeable pads impregnated with an astringent agent.

12 Claims, 14 Drawing Sheets

EAR HYGIENIC IMPLEMENTS AND KIT

CROSS-REFERENCE TO RELATED APPLICATIONS

The present application a Continuation-in-Part (CIP) application of U.S. patent application Ser. No. 16/859,642 filed on Apr. 27, 2020 the disclosure of which is hereby incorporated by reference in its entirety.

FIELD OF THE INVENTION

The present invention relates to personal hygiene, and more particularly, to brushes, sponges, or any cloth swabs for cleaning the ear internally and externally with or without cleaning reagents.

BACKGROUND OF THE INVENTION

Ears provide an opening into the body which opening is susceptible to infiltration by dirt and pathogens. These may be airborne, transferred by finger, introduced by use of audio objects such as cellular phones and head worn microphones, and introduced inadvertently in the course of washing and showering. In addition, ears are sources of bodily secretions as well, such as wax and sweat.

Currently available implements for ear cleaning, such as cotton fiber tipped swabs, inner ear metal and plastic implements, and rubber and silicone implements entail drawbacks. Swabs may push wax and dirt into the inner ear and trapping bacteria deep within the ear canal. Metal and plastic implements can injure ear tissues. Rubber and silicone implements may be partially ineffective as they cannot engage and transport wax and dirt from the inner ear. Liquid ear cleansing drop products also cannot remove solids, and moreover may be messy to use.

There exists a need for an ear cleaning implement providing additional capabilities.

SUMMARY OF THE INVENTION

The present invention provides an ear cleaning implement with enhanced ability to trap and extract solid detritus from the ears, compared to many prior art devices. Notably, the implement selectively includes an open cell foam (i.e. sponge), fabric, or bristle lined cleaning head. This construction both enables distribution of cleansing or therapeutic fluids and also can trap solids for extraction. Both the open cell head and the head bearing bristles may be either permanently fixed to a handle, or removably fixed to the handle. In addition, the cleaning head may include stops or flared sections upon the cleaning head to prevent the cleaning head from being inserted too far into the ear canal, thereby preventing any potential injury.

In addition, a variation of the invention is presented wherein a flexible tube mounted on a stem is utilized for insertion of a cleaning head into the ear canal. The flexible tube houses and compresses a cleaning head in an insertion position and is utilized to provide smooth insertion into the inner ear canal without pushing wax and/or dirt in. Once the flexible tube is inserted, the cleaning head is then advanced out of the flexible tube to an extraction position in the ear canal. In the extraction position, the cleaning head expands to allow for the cleaning of the ear canal as cleaning head is pulled out of the ear canal. Manual (non-electric) and mechanical (electric) versions of this variation are presented.

Each style of cleaning head can engage the handle by elastic contraction or alternatively by interengaging spines or teeth on both the cleaning head and the handle. The portion of the handle engaging the cleaning head may be enlarged in transverse dimension(s).

In an option, the cleaning head may be rotatable and vibrate under electric power.

In a further option, the implement may include two cleaning heads, one at each end of the handle. Where two cleaning heads are provided, the two heads may differ in characteristics such as dimensions, proportions, and specific cleaning surface.

In another option, the implement may include an elongated handle and assembly designed to connect with the elongated handle that serves as a cleaning head. The assembly may have components including a plastic cone, rubber overmold designed to fit over the plastic cone, and sponge designed to fit over the rubber overmold. The plastic cone can attach to the elongated handle by way of a screw-on threaded connection, a pair or pairs of flexible prongs that mate with slits on the plastic cone, or a combination of these. This version of the implement has the advantage of maximum comfort and flexibility while providing an option of interchange, replacement, and separate merchandising of one or more components of the cleaning head assembly and/or the elongated handle, or all of the components of the cleaning head and handle packaged together for assembly by the purchaser.

In a further option, the implement may be part of a kit including hygienic or therapeutic/cleansing fluids and pliable finger held or wrapped-on textured pads (or wipes), impregnated pads for applying hygienic fluids previously impregnated into the pads. The kit may include a spray dispenser for some therapeutic fluids. The kit may also include a bottle of cleaning liquid, gel, foam, paste, or oil to be used with this implement with or without water.

The present invention provides improved elements and arrangements thereof by apparatus for the purposes described which is inexpensive, dependable, and fully effective in accomplishing its intended purposes.

These and other objects of the present invention will become readily apparent upon further review of the following specification and drawings.

BRIEF DESCRIPTION OF THE DRAWINGS

Various objects, features, and attendant advantages of the present invention will become more fully appreciated as the same becomes better understood when considered in conjunction with the accompanying drawings, in which like reference characters designate the same or similar parts throughout the several views, and wherein:

FIG. 15A shows a handle with disk with pronged neck for connecting to the plastic cone of the cleaning head assembly, and FIG. 15B shows handle with disk with threaded portion for connecting to plastic cone of the assembly.

FIG. 17A shows separate components of the cleaning head assembly with sponge and cone and disk that are designed for a screw in attachment, FIG. 17B showing a cone with recess for disk, and FIG. 17C showing a cone with slot for insertion of pronged disk on handle.

FIG. 19A shows a pronged version and FIG. 19B shows a threaded version for attachment to the plastic cone of the cleaning head assembly.

DETAILED DESCRIPTION

Figure 1:
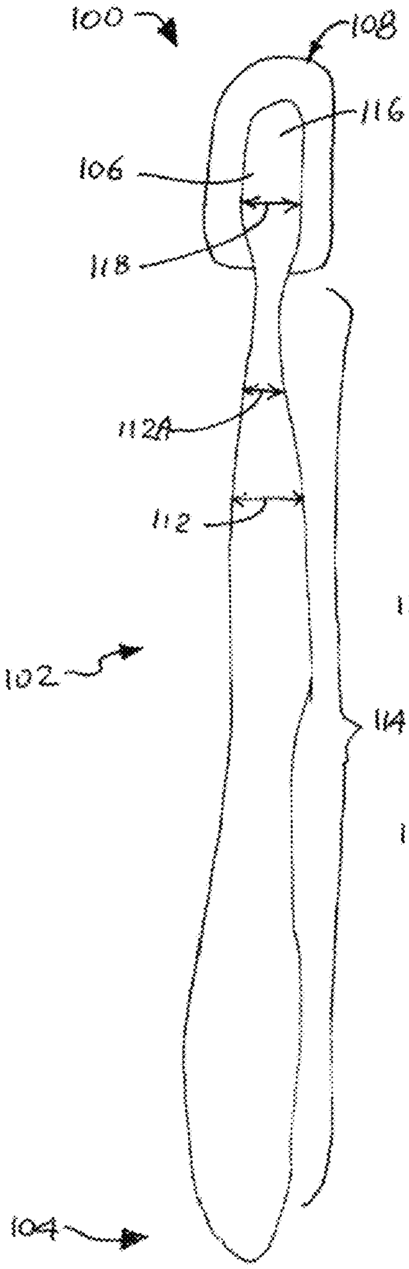
FIG. 1 is a diagrammatic side cross sectional view of an implement for cleaning ears, according to at least one aspect of the invention.

Referring first to FIG. 1, according to at least one aspect of the invention, there is shown an implement 100 for cleaning ears (not shown). Implement 100 may comprise an elongated stem 102 having a proximal end 104 and a distal end 106, and a flexible cleaning head 108 surrounding and coupled to distal end 106 of elongated stem 102. In the embodiment of FIG. 1, elongated stem 102 serves as a handle, and may be curved or contoured as shown to enhance grip characteristics. Therefore, elongated stem 102 may have different transverse dimensions 112 at a handle portion 114 thereof.

It should be noted that proximal and distal ends 104, 106 are semantic devices of convenience, and should not be interpreted narrowly as indicating only the very tips of elongated stem 102. Rather, the term "end" should be understood to encompass some of the length of elongated stem 102.

Figure 2:
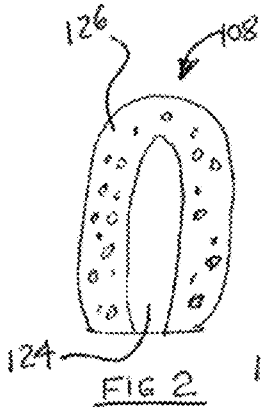
FIG. 2 is a diagrammatic side cross sectional view of a specific form of a component seen at the top of FIG. 1.
Figure 3:
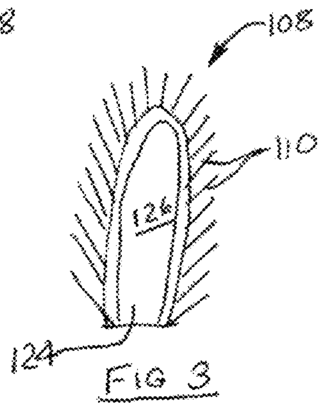
FIG. 3 is a diagrammatic side cross sectional view of an alternative form of the component of FIG. 2.

Shown only generically in FIG. 1, cleaning head 108 may comprise an open cell foam, bristle, cloth or any fabric (FIG. 2). Alternatively, or optionally in addition to the open cell foam, cleaning head 108 may comprise bristles 110 (FIG. 3) projecting outwardly from a hollow base member 126. Hollow base member 126 is a structural member for engaging enlarged head 116 of elongated stem 102, for receiving therapeutic fluids for subsequent application to the ear, and to support second teeth 122 where the latter are used. In the embodiment of FIG. 2, hollow base member 126 comprises open cell foam. FIGS. 2 and 3 illustrate a cavity 124 which may be formed within cleaning head 108 to accommodate insertion of enlarged head 116 of elongated stem 102.

Figure 23:
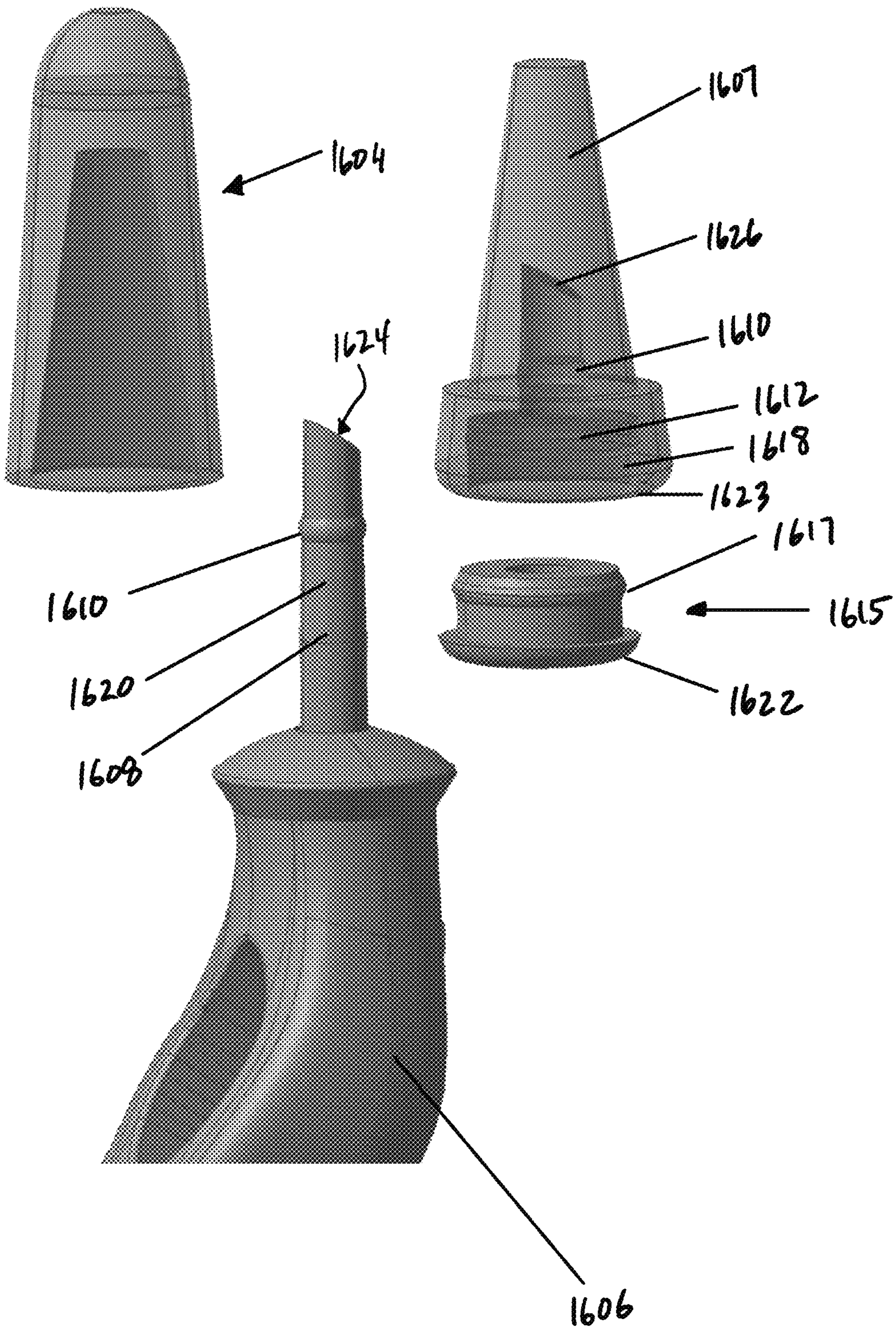
FIG. 23 is a diagrammatic view of an implement for cleaning ears according to another aspect of the invention showing a separate assembly of the disk or ring, cone, overmold, and sponge assembly that can then be added to a handle at a later time.

FIG. 23 is a diagrammatic view of an implement for cleaning ears according to another aspect of the invention, showing a combination of a handle with an elongated stem that includes rib about its circumference that mates with a recess about the inner circumference of the cone or core for attachment of the core to the ribbed handle. The figure also shows a separate ring that includes an enlarged rib about its circumference that mates with a recess about the inner circumference of the cone or core for holding the cleaning head in place to the cone by entrapment.

Unless otherwise indicated, the terms "first", "second", etc., are used herein merely as labels, and are not intended to impose ordinal, positional, or hierarchical requirements on the items to which these terms refer. Moreover, reference to, e.g., a "second" item does not either require or preclude the existence of, e.g., a "first" or lower-numbered item, and/or, e.g., a "third" or higher-numbered item.

Cleaning head 108 may be adhered or configured to removably engage distal end 106 of elongated stem 102. Where cleaning head 108 is configured to removably engage distal end 106 of elongated stem 102 by elastic contraction thereover. This may be a consequence of elastic properties of the open cell foam, the latter being fabricated from a synthetic polymer or from natural sponge material.

In implement 100, elongated stem 102 may have handle portion 114 having transverse dimensions (e.g., as indicated by reference numeral 112), and distal end 106 of elongated stem 102 may comprise an enlarged head 116 having a transverse dimension 118 greater than that of handle portion 114 of elongated stem 102. Of course, handle portion 114 may have transverse dimensions 112 greater in magnitude than transverse dimension 118 of enlarged head 116. In the latter case, elongated stem 102 will have a neck of transverse dimension (e.g., 112A) smaller than either another transverse dimension 112 of elongated stem 102 and enlarged head 116. Enlarged head 116 improves grasp of elongated stem 102 by cleaning head 108.

Figure 4:
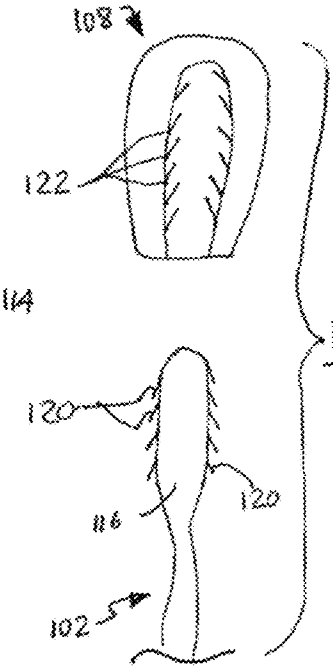
FIG. 4 is a diagrammatic exploded detail view of an embodiment of the implement of FIG. 1.

In an embodiment shown in FIG. 4, cleaning head 108 is configured to removably engage elongated stem 102 by interengagement of respective first teeth 120 of elongated stem 102 and second teeth 122 of cleaning head 108. First and second teeth 120, 122 may be spines or bristles formed integrally with respective elongated stem 102 and cleaning head 108, for example, and may be sufficiently flexible to bend and conform to one another as cleaning head 108 is installed over enlarged head 116. Bending and conforming will contribute to interengagement of teeth 120 and 122 to a degree enabling retention of cleaning head 108 on enlarged head 116 of elongated stem 102.

In the embodiment of FIG. 4, first teeth 120 project away from elongated stem 102 and second teeth 122 project toward elongated stem 102 when cleaning head 108 is installed on elongated stem 102, as seen in FIG. 1.

In an alternative to removable cleaning head 108 of FIGS. 2 and 3, cleaning head 108 may be permanently coupled to distal end 106 of elongated stem 102. This may be accomplished by use of adhesive (not shown), by fusion bonding cleaning head 108 to elongated stem 102, or in any other suitable way.

Figure 5:
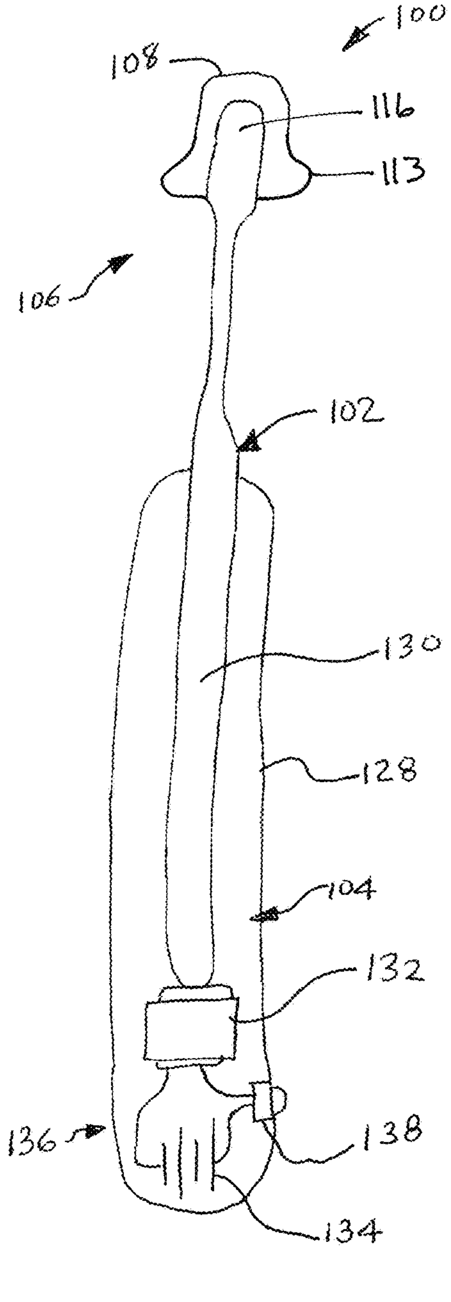
FIG. 5 is a diagrammatic side cross sectional view of a further embodiment of the implement of FIG. 1.

Turning now to FIG. 5, another embodiment is described wherein implement 100 may further comprise a handle 128 surrounding a proximal end portion 130 of elongated stem 102. Elongated stem 102 is rotatable relative to handle 128. Handle 128 includes a motor 132 rotatably drivingly connected to elongated stem 102, and a battery 134 operably connected to motor 132 to provide power to motor 132. Circuitry 136 (indicated in a single line as segments separated by other electrical components) connects motor 132 to battery 134 and includes an on-off switch 138 controlling operation of motor 132. On-off switch 138 may also control rotational speed of motor 132. Rotation of elongated stem 102 enables cleaning head 108 to expeditiously apply therapeutic fluids to the ear canal (not shown), to extract wax and dirt from the ear canal, or both. Vibratory motion of elongated stem 102 is also contemplated as a means to expeditiously apply therapeutic fluids to the ear canal (not shown), to extract wax and dirt from the ear canal, or both. Note that cleaning head 108 in FIG. 5 shows that the cleaning head may include a stop 113 that may be formed, molded or added to the cleaning head 108. Stop 113 is a flared portion that prevents the cleaning head 108 from being inserted too deeply into the ear canal by the user and can be added to in any of the embodiments shown herein.

Figure 6:
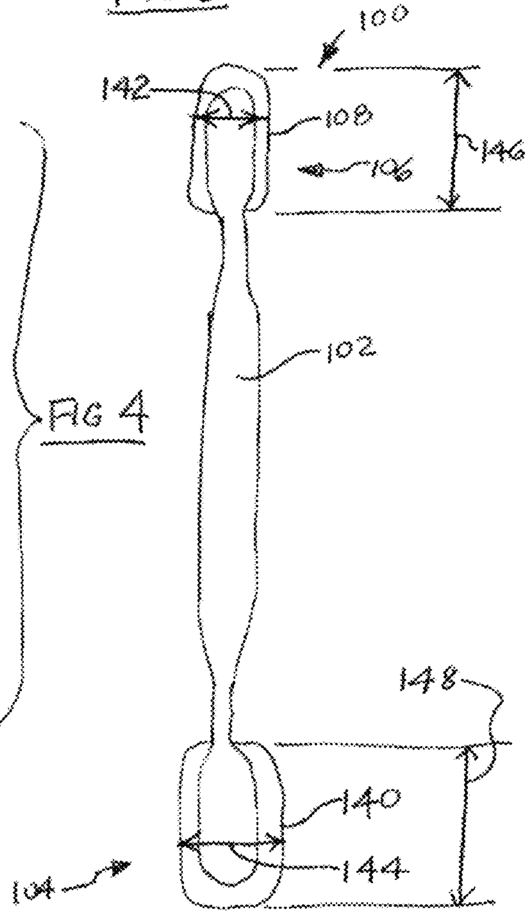
FIG. 6 is a diagrammatic side cross sectional view of still another embodiment of the implement of FIG. 1.

Turning now to FIG. 6, there is shown an embodiment of implement 100 wherein flexible cleaning head 108 is a first flexible cleaning head, and implement 100 further comprises a second cleaning head 140 at proximal end 104 of elongated stem 102. First cleaning head 108 has first surface characteristics and second cleaning head 140 has second surface characteristics different from the first surface characteristics of first flexible cleaning head 108. This enables implement 100 of FIG. 6 to accommodate a wider variety of scrubbing and cleaning techniques than that of FIGS. 1 and 5.

In implement 100 of FIG. 6, the first surface characteristics may include a first transverse dimension 142, and the second surface characteristics may include a second transverse dimension 144 different from first transverse dimension 142. Independently of transverse dimensions 142 and 144, the first surface characteristics may include a first length, width and shape 146, and the second surface characteristics may include a second length, width and shape 148 different from first length, width and shape 146. The shapes and contours of first and second cleaning heads 108 and 140 may also differ from each other. Still other characteristics may differ between first and second cleaning heads 108 and 140. For example, first and second cleaning heads 108 and 140 may both comprise open cell foam, but have different pore sizes. In a further example, first and second cleaning heads 108 and 140 may both have bristles 110, but of different lengths, flexibility, and/or thicknesses.

The first surface characteristics may include a first matter retainer (e.g. bristles) and the second surface characteristics may include a second matter retainer (e.g. bristles of different diameter, stiffness, or spacing) different from the first matter retainer. The first matter retainer may comprise open cell foam of one pore size or flexibility, while the second matter retainer may have different pore size or flexibility. A matter retainer is a cleaning head 108 (or 140) having structure for trapping ear wax, dirt, and other solid matter in the ear and retaining the solid matter while withdrawing implement 100 from the ear.

Exemplary dimensions of implement 100 include an overall length (from proximal end 104 to distal end 106) of seven to eight inches. Transverse dimensions of elongated stem may range from three sixteenths of an inch to three quarters of an inch. Wall thickness of cleaning head 108, where comprising open cell foam (FIG. 2), may range from one eighth of an inch to three eighths of an inch, and may vary within this range at different degrees of rotation about the length (i.e., the front view may show different wall thicknesses from a side view). Where used, bristles 110 may vary similarly. Enlarged head 116 may vary in transverse dimensions as well. Exemplary dimensions reflect preferred embodiments, but do not limit dimensional possibilities.

Figure 8:
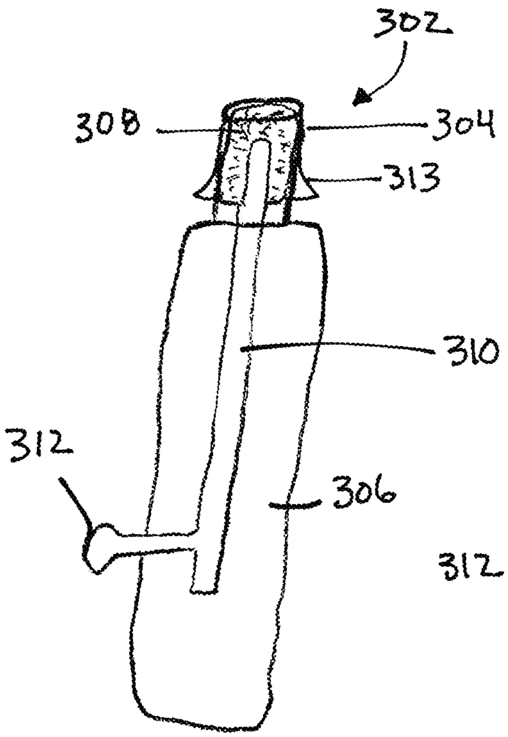
FIG. 8 is a diagrammatic view of an implement for cleaning ears according to another aspect of the invention, shown in a first position.
Figure 9:
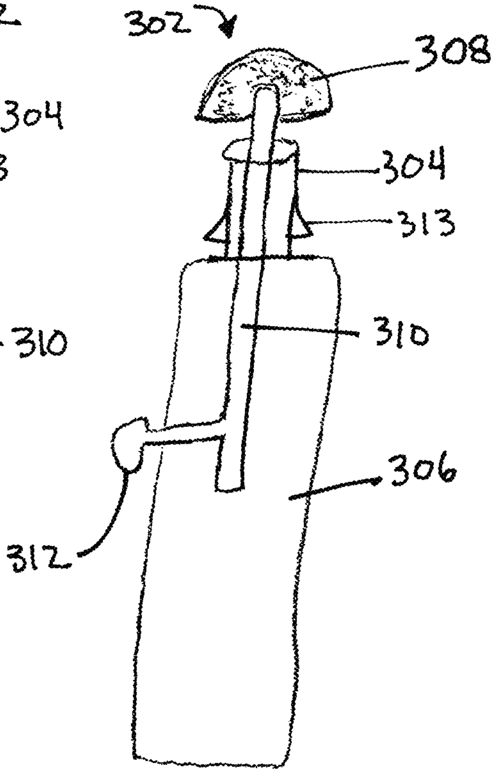
FIG. 9 is a diagrammatic view of an implement for cleaning ears in FIG. 8 shown in a second position.

Turning now to FIGS. 8 and 9, presented therein is an additional embodiment of an implement for cleaning ears 302. In this variation, flexible tube 304, preferably made of silicon, is mounted on a body that acts as a handle 306. In FIG. 8, it can be seen that the flexible tube 304 houses and compresses a cleaning head 308 in an insertion position and is utilized to provide smooth insertion into the inner ear canal without pushing wax and/or dirt in. Once the flexible tube is inserted into the ear canal, the cleaning head 308 is then advanced out of the flexible tube to an extraction position in the ear canal. In the extraction position shown in FIG. 9, the cleaning head 308 expands to allow for the cleaning of the ear canal as the cleaning head is pulled out of the ear canal. FIGS. 8 and 9 depict a manual embodiment of the implement for cleaning ears 302. In this embodiment, the operation of the cleaning head in and out of the flexible tube 304, is provided by rod 310 that is fixed to the cleaning head 308 and extends into the handle 306. Movement of the rod 310 is provided by finger slide 312 that is functionally connected to rod 310. Finger slide 312 is retained in a channel (not shown) that includes stops at each travel extreme such that the travel of the rod 310 is confined between the two extremes to avoid potential injury to the user. In addition, flexible tube 304 may include a stop 313 that may be molded in the tube or added to the tube. Stop 313 is a flared portion that prevents the tube 304 from being inserted too deeply into the ear canal by the user.

Figure 10:
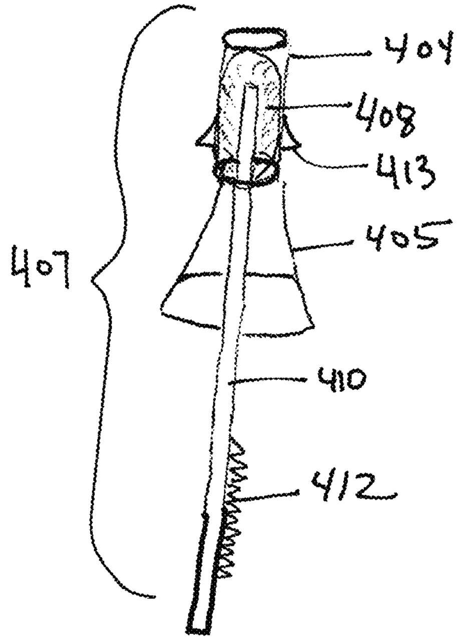
FIG. 10 is a diagrammatic view of an implement for cleaning ears according to another aspect of the invention, shown in a first position.
Figure 11:
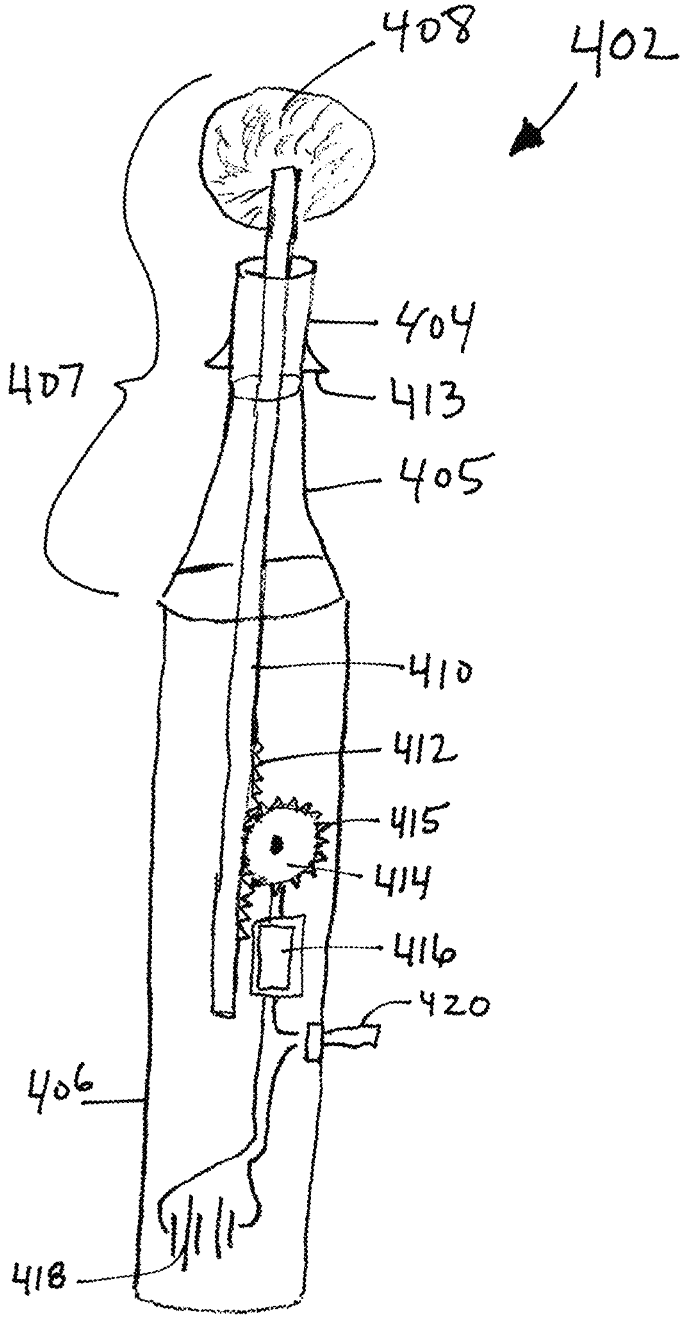
FIG. 11 is a diagrammatic view of an implement for cleaning ears in FIG. 10 shown in a second position.

Turning now to FIGS. 10 and 11, presented therein is an additional embodiment of an implement for cleaning ears 402. Again, in this variation a flexible tube 404, preferably made of silicon, is mounted on a stem 405 which detachably connects to a body that acts as a handle 406. In FIG. 10, it can be seen that the flexible tube 404 houses and compresses a cleaning head 408 in an insertion position and is utilized to provide smooth insertion into the inner ear canal without pushing wax and/or dirt in.

Shown in FIG. 10 is the detachable component 407 of ear cleaning implement 402 that includes the flexible tube 404, the stem 405, and a compressed cleaning head 408 that is fixed to rod 410. As can be see, rod 410 includes a teethed portion 412.

In the extraction position shown in FIG. 11, the cleaning head 408 expands to allow for the cleaning of the ear canal as the cleaning head is pulled out of the ear canal. FIGS. 10 and 11 depict an electronic/motorized embodiment of the implement for cleaning ears 402. In this embodiment, the operation of the cleaning head in and out of the flexible tube 404, is provided by rod 410 that is fixed to the cleaning head 408 and extends into the handle 406. Movement of the rod 410 is provided by gear 414 that is rotated by motor 416 that is powered by an energy source 418 (ex. battery). Gear 414 includes a teethed surface 415 that matingly engages with the teethed portion 412 of the rod 410. A toggle switch 420 is electronically connected to the energy source 418 and motor 416 such that the user can control the movement of the cleaning head 408 in and out of the flexible tube 404. Note that the ear cleaning implement 402 may include structural or electronically managed stops (not shown) that includes stops at each travel extreme such that the travel of the rod 410 is confined between the two extremes to avoid potential injury to the user. In addition, flexible tube 404 may include a stop 413 that may be molded in the tube or added to the tube. Stop 413 is a flared portion that prevents the tube 404 from being inserted too deeply into the ear canal by the user.

Figure 7:
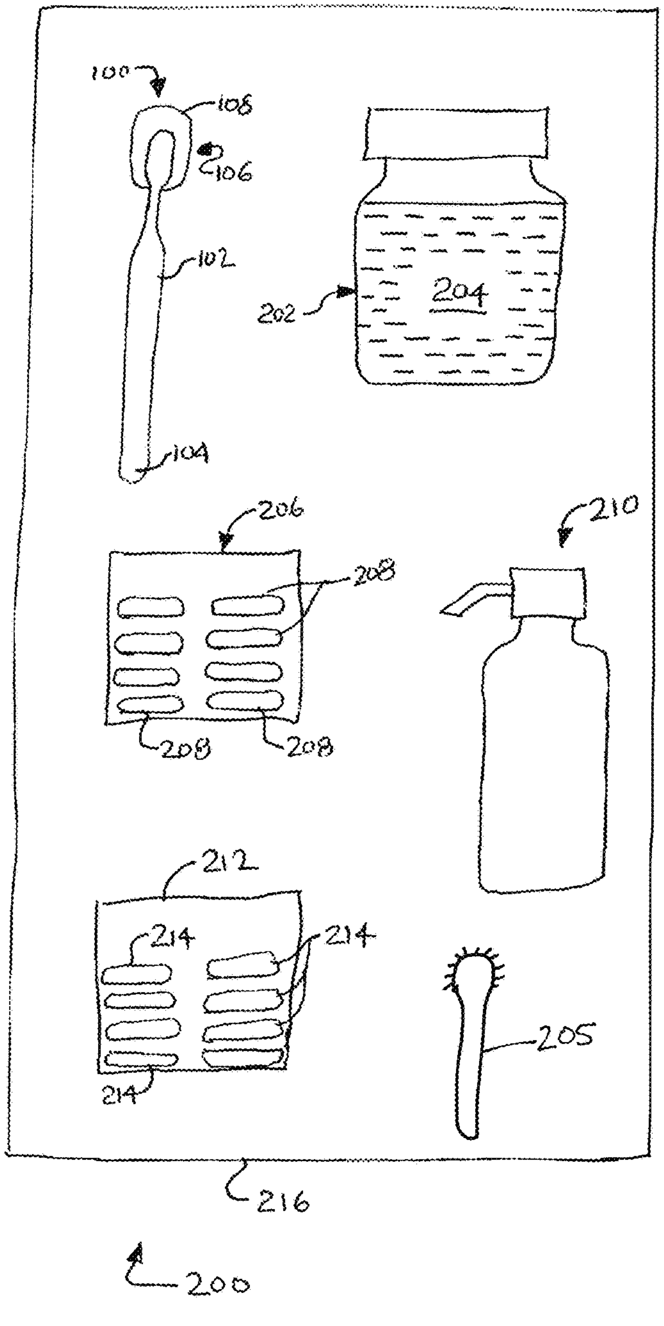
FIG. 7 is a diagrammatic view of components of a kit including any of the embodiments of the implement of FIG. 1 and other components.

Referring primarily to FIG. 7 but also to FIGS. 1-6 and FIGS. 8-11, the invention may be practiced as a kit 200 for cleaning the ears.

EAR SPONGE—Kit 200 may comprise implement 100 (302 or 402) for cleaning ears, implement 100 comprising elongated stem 102 having proximal end 104 and distal end 106, and a flexible liquid permeable cleaning head (e.g., cleaning head 108) surrounding and coupled to distal end 106 of elongated stem 102.

EAR FOAM—Kit 200 may also include a container 202 containing any cleansing/therapeutic agents—gel, paste, liquid, cream, mousse or oil foam 204, oil foam 204 comprising oil, soap, for use with or without and water (ingredients not separately shown). Treating flaky ears, swimmer ear, ear pimples MOISTURIZING DEODORIZING EAR MYST—Kit 200 may also include a spray container 210 containing antibacterial moisturizing deodorizing and therapeutic liquid (not separately shown).

EAR SCRUB WIPES—Kit 200 may also include a package 206 containing a supply of first liquid permeable pads 208 impregnated with antibacterial and therapeutic liquid (not separately shown).

MOISTURIZING DEODORIZING EAR WIPES—Optionally, kit 200 may further comprise a container 212 containing a supply of second liquid permeable pads 214 impregnated with an astringent deodorizing agent (not separately shown).

EAR WIPE HANDLE—Also a hand-held implement 205 for wipes. Having textured teeth or Velcro head so wipes can stick on it rather than the user using their fingers to hold the wipes.

As employed herein, the term "supply" is to be interpreted as a plurality of pads 208 or 214 in a number suitable for consumer use by one person, such as two to fifty pads 208 or 214 in the course of routine retail sales for example. It should be recognized that kit 200 may be intended for use with plural patients, e.g., by a health facility or by health personnel responding to a local emergency event, and could therefore comprise more than fifty pads 208 or 214.

Kit 200 may include the following therapeutic liquids mentioned above. Antibacterial liquid may comprise in an aqueous or oil base, bacitracin, neomycin, other known bactericidal agents, and combinations of these. The astringent agent may comprise witch hazel moisturizing glycerin deodorizing essential oils for example.

Components of kit 200 described above are enclosed within a common enclosure 216. The latter may be any type of packaging suitable for shipping or for retail and capable of protecting components of kit 200 from casual damage and contamination, for example.

Additional embodiments of ear cleaning implements will be described in the following figures. The additional ear cleaning implements have a plastic handle that can connect or disconnect with an assembly that serves as a cleaning head. The cleaning head assembly has a plastic cone core that removably attaches to a disk on the handle directly or by way of a separate disk that connects the handle and plastic cone core (or other rounded shape) together, a rubber overmold that fits over the plastic cone core, and an outer removeable sponge that makes contact with the ear canal interior, outer ear, and behind ear during use. The implements can use one or more attachment mechanisms including a paired male-prong, female-slit mated connection, a screw-on threaded connection, or various combinations of these. The prongs can take the form of one or more pairs made flexible to interlock with the plastic cone core by way of engagement members or projections protruding at right angles from the top of the prongs which latch onto the sides of the cone at the bottom of slits in the sides of the cone. The engagement members or projections of the prongs can have a triangular cross-section that has a first surface which is slanted that allows the prongs to slide into and enter the plastic cone through an aperture at the bottom of the cone that is continuous with the slits while providing a second surface disposed at a right angle to the prongs that engages a surface of the cone at the bottom of the slits to lock the prongs in place. Another option is where the cone can be in two pieces where the pieces can be halved along the longitudinal access and where by the engagement to the prongs is via snap-fitting the two-halves together about the prongs. The cleaning head is designed for maximum comfort, pliability, and safety and provides for replaceable components such as sponges or soft bristles that can be replaced or cleaned with each use as well as other components that can be exchanged if damaged or lost. Suitable plastic materials include polymers such as acrylic, polycarbonate, polyethylene, polypropylene, and polyvinyl chloride. The plastic materials can be chosen for characteristics such as rigidity and flexibility according to the role of each component, such as greater flexibility when forming the prongs. The handle can also be made of a metal, wood, plastic or metal alloy that provides for flexible prongs. The plastic components can be manufactured through processes such as injection molding, extrusion, thermoforming, and three-dimensional printing. Suitable rubber materials include synthetic rubber such as butadiene, styrene-butadiene, butyl rubber, neoprene and silicone, as well as natural rubber.

Figure 12A:
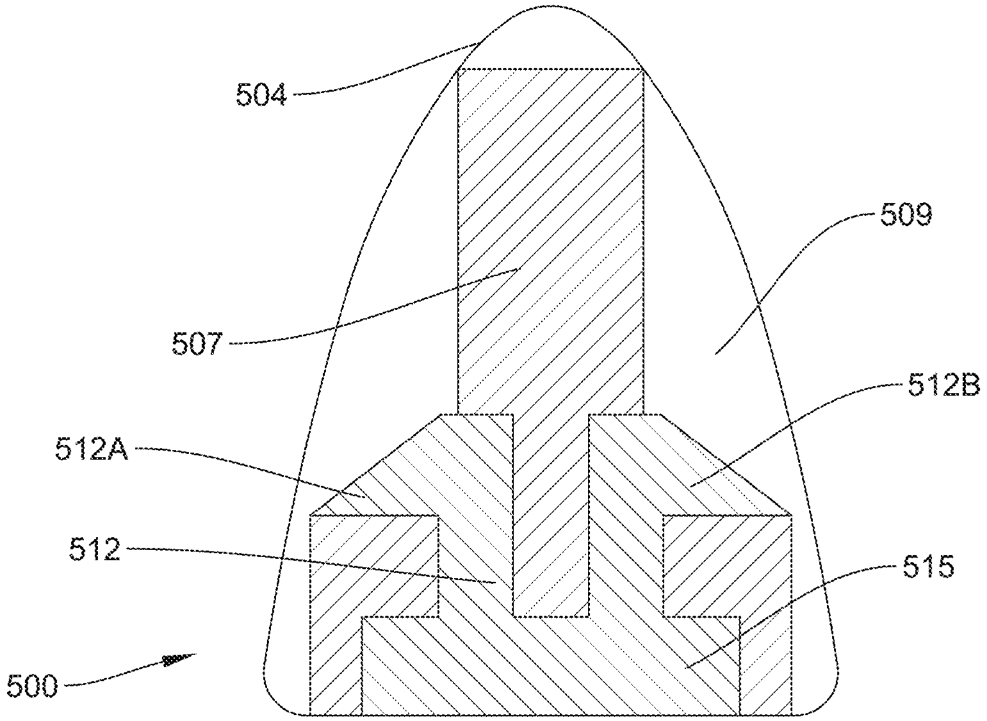
FIGS. 12A-12C are diagrammatic views of an implement for cleaning ears according to another aspect of the invention, with FIG. 12A showing a cleaning head assembly and FIGS. 12B and C showing front and lateral cross-sections of a plastic cone of the assembly of FIG. 12A.
Figure 12B:
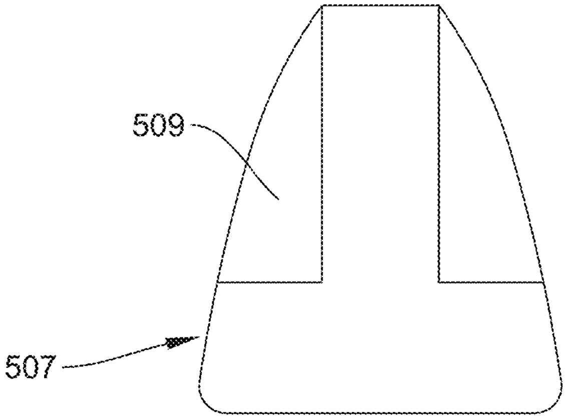
Figure 12C:
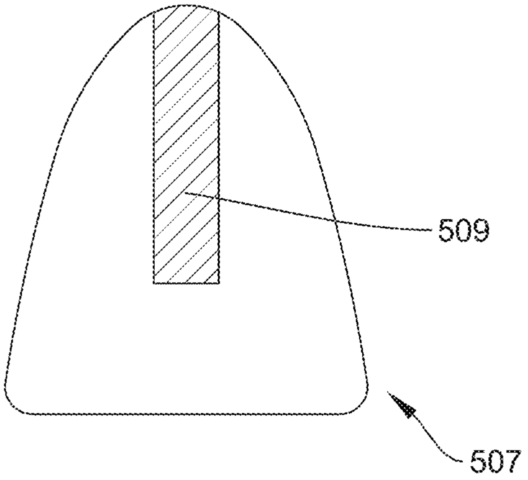
Figure 13A:
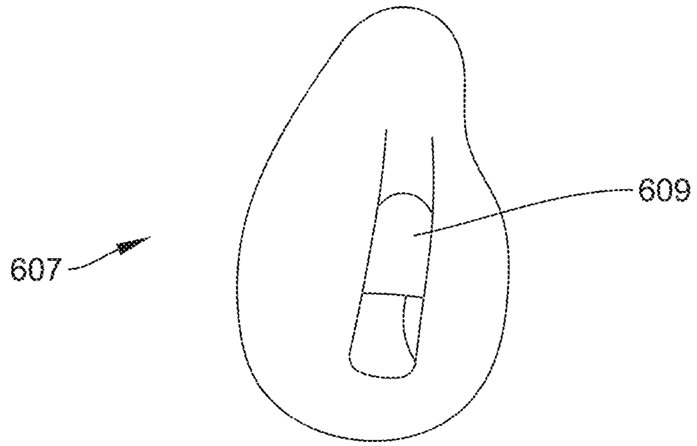
FIGS. 13A-13C are images showing a putty model of a plastic cone of the assembly with slits.
Figure 13B:
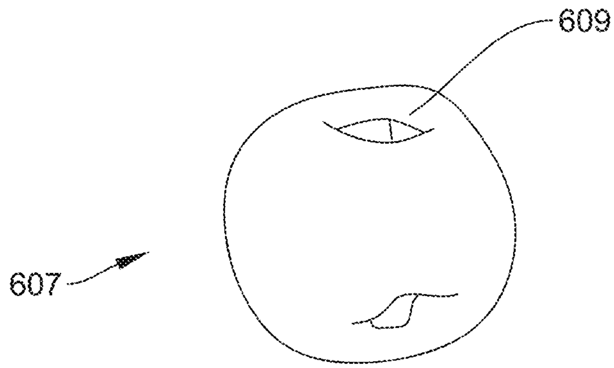
Figure 13C:
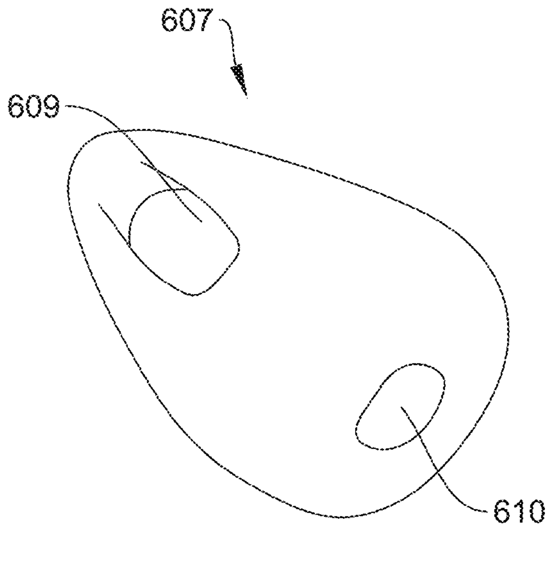
Figure 14A:
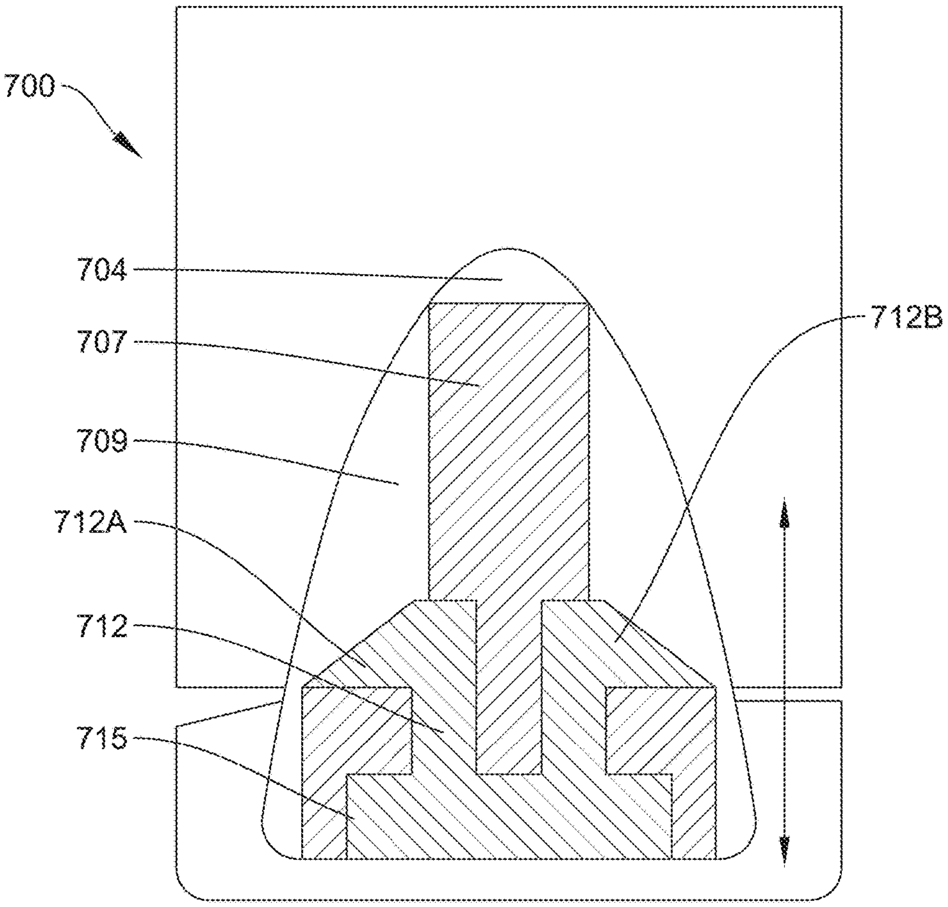
FIGS. 14A-14D are diagrammatic views of an implement for cleaning ears according to another aspect of the invention, with FIG. 14A showing a cleaning head assembly, FIGS. 14B and 14C showing front and lateral cross-sections of a plastic cone of the assembly of FIG. 14A, and FIG. 14D showing a disk with pronged neck for attachment to the assembly.
Figure 14B:
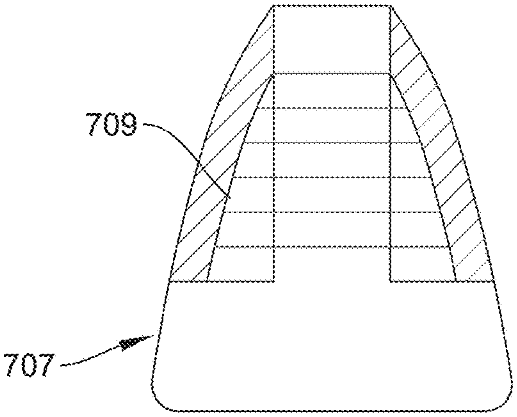
Figure 14C:
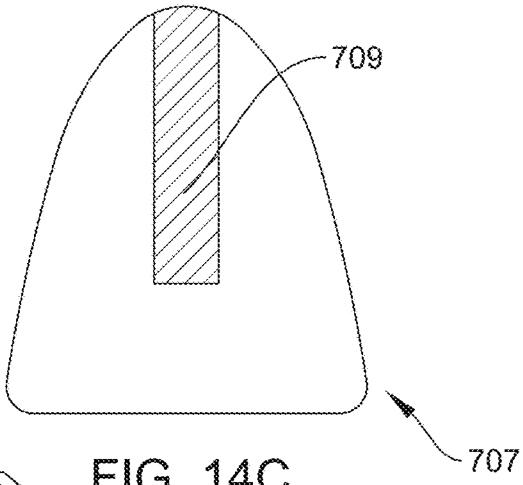
Figure 14D:
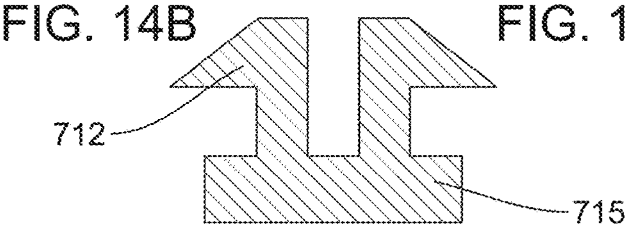

Turning now to FIGS. 12A-12C, an implementation of a cleaning head assembly 500 is shown. A disk 515 having a pair of prong members 512 protruding from top of disk 515 is mated with plastic cone 507 by way of slots 509 that receive prong members 512. Projections with triangular cross-section (e.g., symmetrical right triangles 512A and 512B) project at right angles out of top of each of the prong members 512 to latch into slots 509. A rubber overmold 504 covers the plastic cone to complete the assembly. Overmold 504 may be applied to the cone or core 507 either as a separate part or in the injection process. Not shown is sponge portion which will be shown in subsequent figures. FIGS. 12B and 12C show cross sections of cone 507 with two slots 509 on either side of plastic cone, with FIG. 12B showing a front cross-section and FIG. 12C showing a lateral cross-section. FIGS. 13A-13C also illustrate model of plastic cone or core 607 with two slots 609 running along either side of cone 607. The projections of the prong (not shown) enter cone through bottom hole 610 of cone and attach to cone 607 at slots 609 which are continuous with aperture 610. FIGS. 14A-14D show the assembly 700 with disk 715 having pair of prong members 712 protruding from top of disk 715 mated with plastic cone or core 707 by way of slots 709 that receive prong members 712 including engagement members or projections 712A and 712B with triangular cross-section protruding outward from top of prong 712 at right angles. A rubber overmold 704 covers the plastic cone. Pair of vertical arrows in FIG. 14A show how the overmold 704 is able placed on cone 707 if assembled as a separate part and not attached to the cone 707 during the injection process. Front (FIG. 14B) and lateral (FIG. 14C) cross-sections of the plastic cone are shown as well as a cross-section of the pronged disk component 712 in FIG. 14D.

Figure 15A:
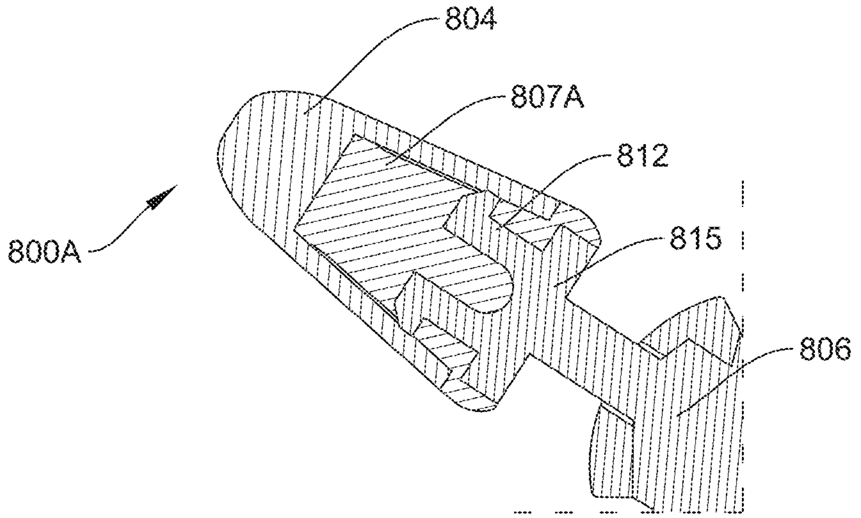
FIGS. 15A and 15B are diagrammatic views of an implement for cleaning ears according to additional aspects of the invention, where
Figure 15B:
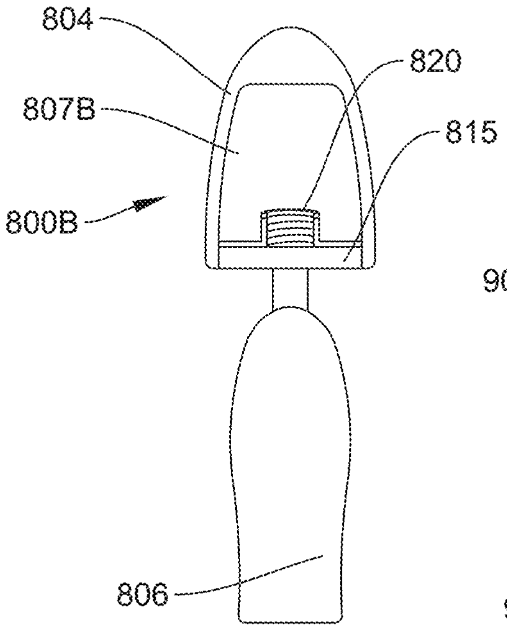
Figure 16:
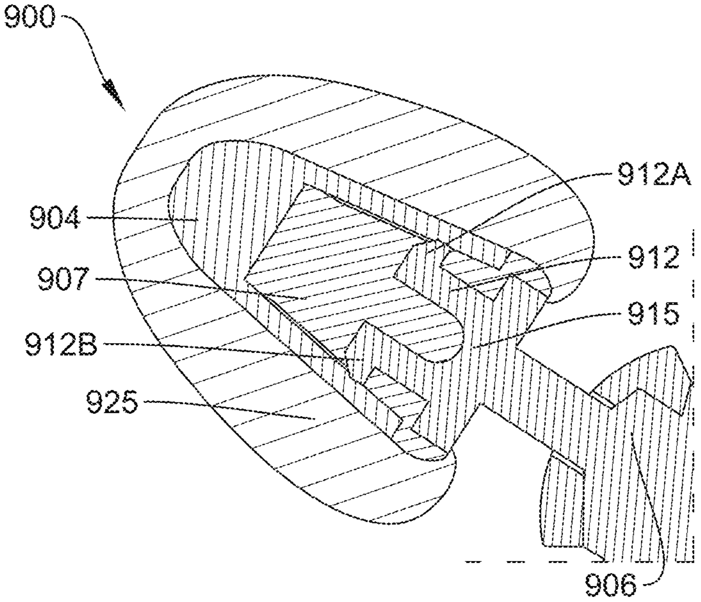
FIG. 16 is a diagrammatic view of an implement for cleaning ears according to another aspect of the invention, where sponge is fitted over rubber overmold of the cleaning head assembly.

Turning now to FIGS. 15A and 15B, two different implementations of assemblies 800A and 800B are shown. FIG. 15A shows a version of plastic cone or core 807A that has bilateral slits to accept flexible prongs 812 protruding from disk 815 of handle 806, while FIG. 15B shows plastic cone or core 807B that is screwed on through threaded member 820 on disk 815. Disk 815 extends from top of handle 806 of the device. Rubber overmold 804 is also the same on both implementations. FIG. 16 shows a magnified view of assembly 900 attached to handle 906 by way of disk 915 having two flexible prongs 912 protruding above and having engagement members 912A and 912B that protrude at right angles to fit and latch into slots in plastic cone or core 907. The rubber overmold 904 fits over the plastic cone 907 and a sponge 925 is fitted over the rubber overmold 904. The sponge 925 is entrapped between the plastic cone 907 and the disk 915 by way of recess in cone 907 that acts to entrap the sponge 925 between the plastic cone 907 and the disk 915 to help hold it in place. The rubber overmold 904 acts to provide cushion to the sponge 925 to make it more pleasant to use, and is textured to provide a frictional surface to help hold the sponge 915 in place.

Figure 17A:
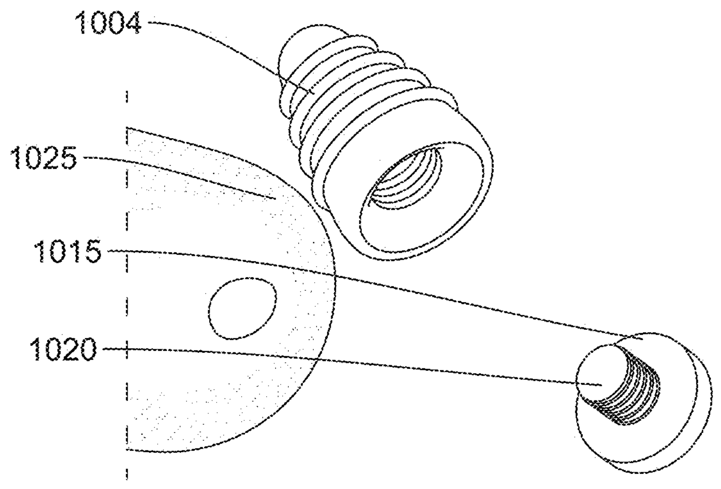
FIGS. 17A-17C are images of an implement for cleaning ears according to additional aspects of the invention where
Figure 17B:
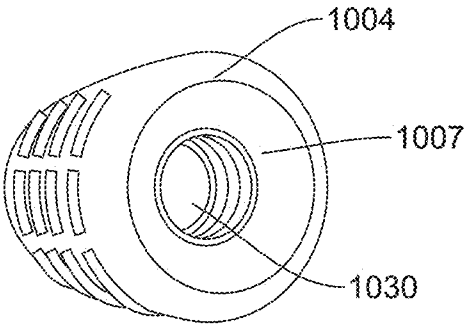
Figure 17C:
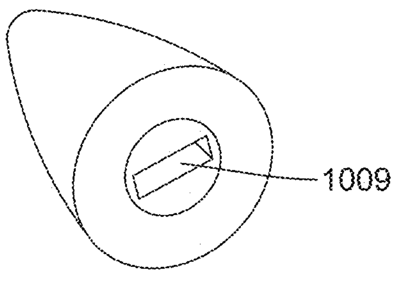
Figure 18A:
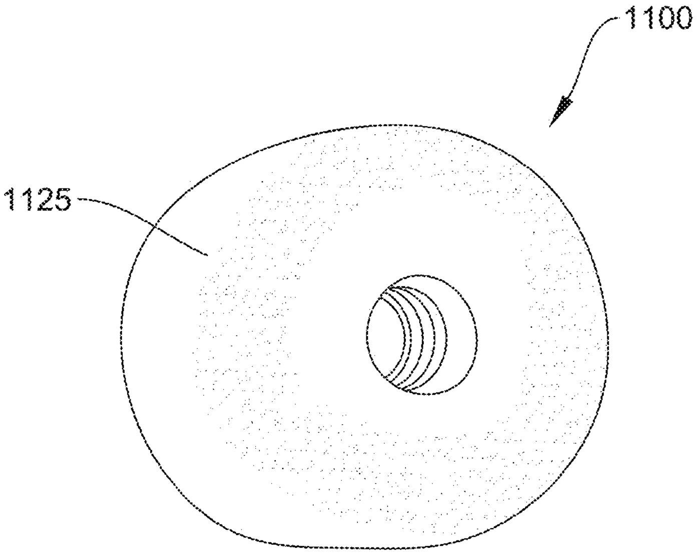
FIGS. 18A and 18B are images of an implement for cleaning ears according to additional aspects of the invention where a completed cleaning head assembly with a sponge over the plastic cone and rubber overmold are shown in FIG. 18A and the completed assembly attached to the handle with sponge entrapped by recess in the cone by the disk is shown in FIG. 18B.
Figure 18B:
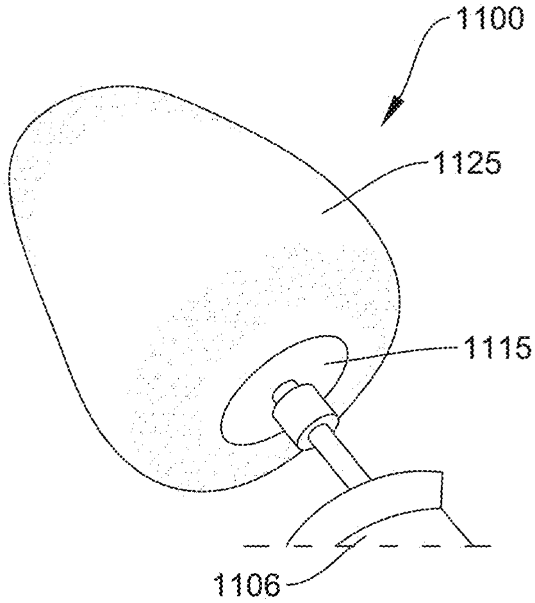
Figure 19A:
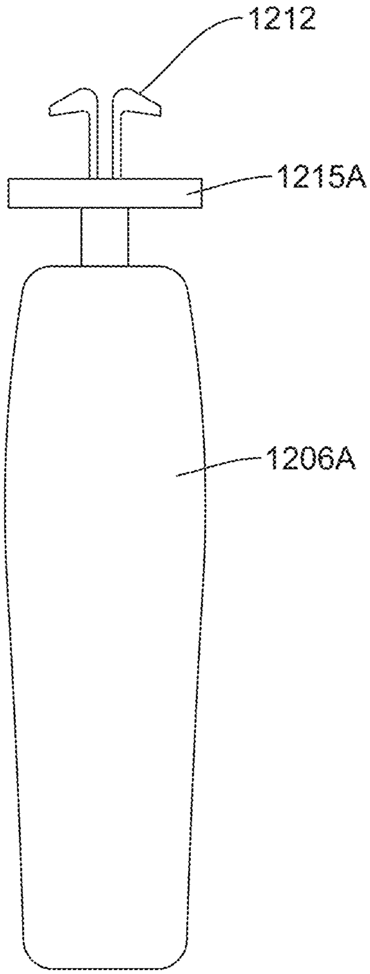
FIGS. 19A and 19B are diagrammatic views of two different implementations of a handle for an implement for cleaning ears, where
Figure 19B:
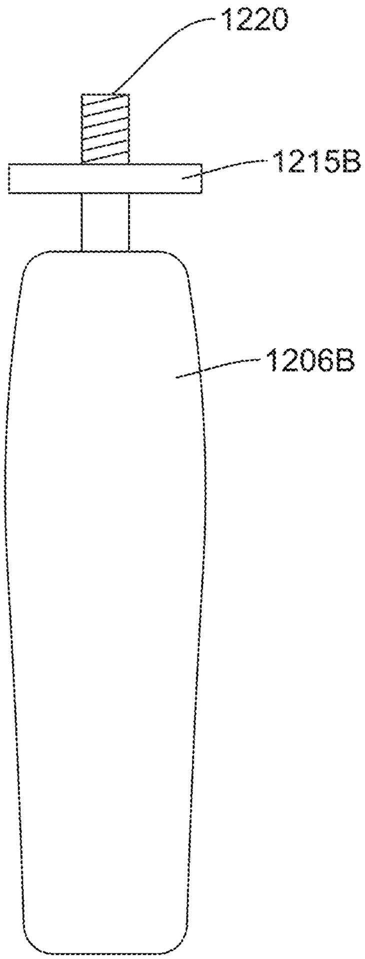

FIGS. 17A and 17B show an assembly with plastic cone 1007, rubber overmold 1004 over cone, disk 1015, and sponge 1025 which is to be placed over rubber overmold 1004. In this instance the disk 1015 has a threaded portion 1020 that screws into threads 1030 of cone 1007. FIG. 17C shows bottom of cone with slot 1009 for insertion of pronged disk on handle (not shown). The cone has a recess that acts to entrap the sponge between the cone and the disk to help hold it in place. FIGS. 18A and 18B show cleaning head assembly 1100 with the sponge 1125 covering the plastic cone and rubber overmold underneath. The sponge 1125 is entrapped in the recess of the cone by the disk 1115 connected to the handle 1106, as shown in FIG. 18B. The assembly 1100 is screwed to the handle 1106 by disk 1115. FIGS. 19A and 19B show two different versions of the handle 1206A and 1206B, one with flexible prongs 1212 protruding from disk 1215A, and one with threaded portion 1220 protruding from center of disk 1215B, which provide two different connection mechanisms for attaching cleaning head assembly to handle.

Figure 20:
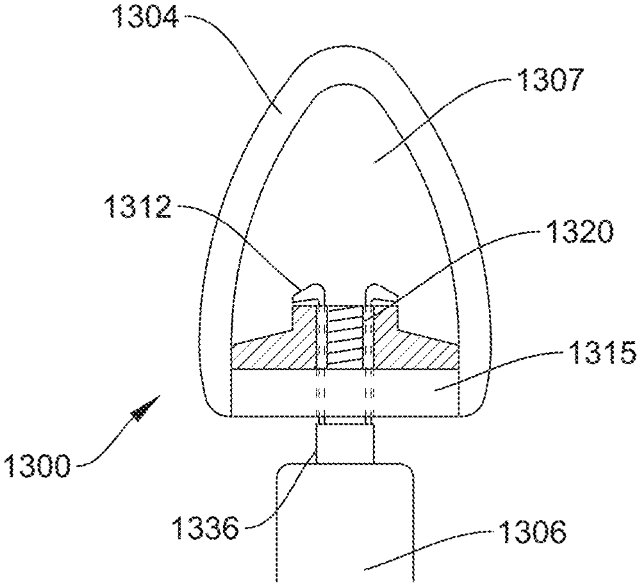
FIG. 20 is a diagrammatic view of an implement for cleaning ears according to another aspect of the invention, showing a combination of a pronged handle and separate threaded disk for attachment to the plastic cone of the cleaning head assembly.
Figure 21:
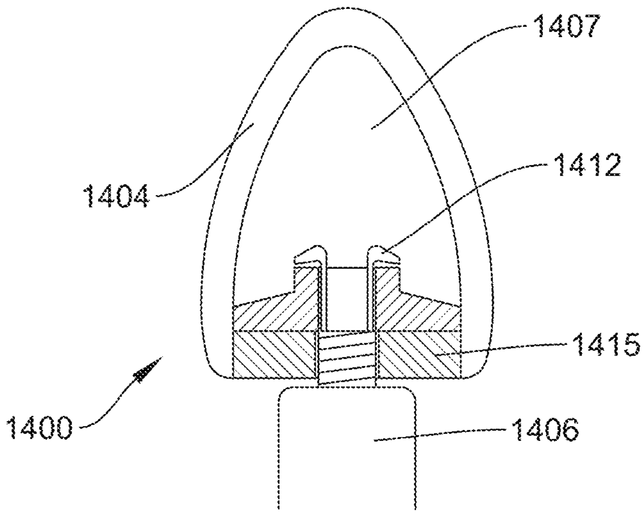
FIG. 21 is a diagrammatic view of an implement for cleaning ears according to another aspect of the invention, showing a combination of a threaded handle and separate pronged disk for attachment to the plastic cone of the cleaning head assembly.
Figure 22A:
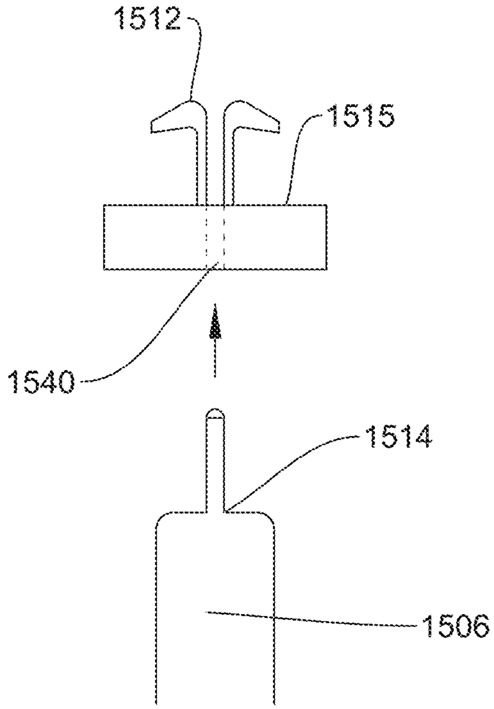
FIGS. 22A and 22B are diagrammatic views of an implement for cleaning ears according to another aspect of the invention, showing a pronged handle attached to a separate pronged disk, both of which attach to the plastic cone of the cleaning head assembly by way of two orthogonal pairs of slits.
Figure 22B:
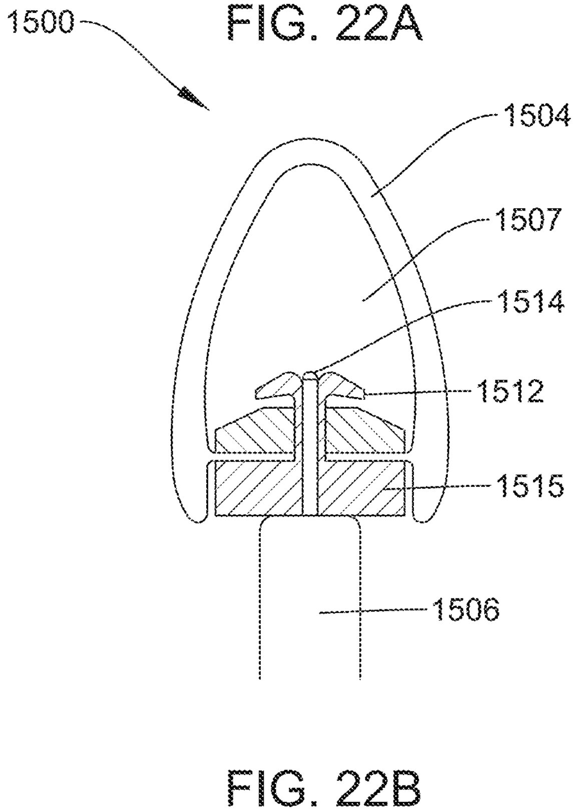

The following variations allow for a separate assembly of the disk/cone/overmold/sponge that can then be added to a handle at a later time. The variations include a separate disk that acts as an intermediate connector for attaching the handle to the cleaning head assembly. FIG. 20 illustrates a cleaning head assembly 1300 having a separate screw in disk 1315 that mates with threaded sides 1320 of interior portion of cone 1307. Slits in the cone 1307 receive flexible prongs 1312 of the handle 1306 while the screw disk 1315 holds the assembly 1300 together. The screw disk 1315 has openings 1336 or a slit or hole in its core for the flexible prongs 1312 that would allow for the two-pronged handle 1306 to be inserted to hold the assembly 1300 on the handle. The rubber overmold 1304 is shown over the plastic cone 1307. FIG. 21 shows a different implementation with a threaded handle 1406 and separate pronged disk 1415 used to hold the assembly 1400 including rubber overmold 1404 and plastic cone 1407 together. The flexible prongs 1412 of the disk 1415 mate with slits in the cone 1407. The disk 1415 has a threaded core that screws onto the threaded handle 1406 to connect the assembly 1400 and handle 1406 together. In another implementation, shown in FIGS. 22A and 22B, a separate pronged disk 1515 mates with a slotted cone 1507 as described above, where the pronged disk 1515 holds the assembly 1500 including rubber overmold 1504 together, but also attaches to a pronged handle 1506. To attach the assembly 1500 to the pronged handle 1506, an additional pair of slits are placed in the plastic cone 90 degrees to the first pair of slits (used for the disk prongs 1512) as well as a slit or hole 1540 in the pronged disk that receives handle prongs 1514 to attach the assembly 1500 to the handle 1506. As such, the cone 1507 has four slits for the two pairs of flexible prongs 1512, 1514, each slit 90 degrees from the adjacent slits, such that the two pairs are orthogonal to each other. In another version, the two pairs of slits are provided at different heights of the cone 1507 to minimize overlap, such as two top slits for the disk prongs 1512 and two lower slits for the handle prongs 1514.

The following variations shown in FIG. 23 allow for a separate assembly of the disk or ring, cone, overmold, and sponge assembly that can then be added to a handle at a later time. The variations shown in FIG. 23 include a combination of a handle 1606 with an elongated stem 1608 that includes rib 1610 about its circumference 1620 that mates with a recess 1610 about the inner circumference of the cone or core 1607 for attachment of the core 1607 to the ribbed 1610 elongated stem 1608 of the handle 1606 Note that the elongated stem 1608 terminates in an angled surface 1624, which when inserted and seated in the cone 1607 at complementary surface 1626, prevents the cone 1607 from rotating on the on the elongated stem 1608. The figure also shows a separate ring 1615 that includes an enlarged rib 1617 about its circumference that mates with a recess 1612 about the inner circumference 1618 of the cone or core 1607 for holding the cleaning head (not shown) in place to the cone 1607 by entrapment between the ring ridge 1622 and cone 1607 outer surface 1623. Also pictured is overmold 1604 that covers the surface of cone 1607 when assembled.

The invention of FIGS. 12A-12C, 13A-13C, 14A-14D, 15A and 15B, 16, 17A-17C, 18A and 18B, 19A and 19B, 20, 21, and 22A and 22B and 23 can be practiced as a kit or as a component of a kit as with preceding embodiments, as those skilled in the art will appreciate, including an ear sponge implement for cleaning ears, ear foam, moisturizing deodorizing ear mist, ear scrub wipes, moisturizing deodorizing ear wipes, and ear wipe handle, as described above, and/or can include one or more features specified in the preceding embodiments.

While the present invention has been described in connection with what is considered the most practical and preferred embodiment, it is to be understood that the present invention is not to be limited to the disclosed arrangements, but is intended to cover various arrangements which are included within the spirit and scope of the broadest possible interpretation of the appended claims so as to encompass all modifications and equivalent arrangements which are possible.

I claim:

1. An implement for cleaning ears, the implement comprising:
- an elongated handle terminating at a pair of prongs protruding vertically therefrom, each prong terminating at an engagement member projecting horizontally from the prong at a right angle;
- a disk having a threaded side and an aperture designed to receive the pair of prongs; and
- cleaning head assembly components comprising:
  - a plastic cone having a bottom threaded opening designed to screw onto the threaded side of the disk and a pair of bilateral slits designed to receive the pair of prongs;
  - a rubber overmold over the plastic cone; and
  - a sponge designed to fit over the rubber overmold.

2. The implement of claim 1, wherein the plastic cone has a recess designed to entrap the sponge between the plastic cone and the disk.

3. The implement of claim 1, wherein the rubber overmold is attached to the plastic cone.

4. The implement of claim 1, wherein each engagement member has a triangular cross section.

5. An implement for cleaning ears, the implement comprising:
- an elongated handle terminating at a threaded portion protruding vertically therefrom;
- a disk having a bottom threaded opening designed to screw onto the threaded portion of the elongated handle and a pair of prongs protruding vertically from the disk, each prong terminating at an engagement member projecting horizontally from the prong at a right angle; and
- cleaning head assembly components comprising:
  - a plastic cone having a bottom aperture and pair of bilateral slits designed to receive the pair of prongs;
  - a rubber overmold designed to fit over the plastic cone; and
  - a sponge designed to fit over the rubber overmold.

6. The implement of claim 5, wherein the plastic cone has a recess designed to entrap the sponge between the plastic cone and the disk.

7. The implement of claim 5, wherein the rubber overmold is attached to the plastic cone.

8. The implement of claim 5, wherein each engagement member has a triangular cross section.

9. An implement for cleaning ears, the implement comprising:
- an elongated handle terminating at a first pair of prongs protruding vertically therefrom, each prong of the first pair of prongs terminating at an engagement member projecting horizontally from the prong at a right angle;
- a disk having a bottom aperture designed to receive the first pair of prongs and having a second pair of prongs protruding vertically from the disk, each prong of the second pair of prongs terminating at an engagement member projecting horizontally from the prong at a right angle;
- cleaning head assembly components comprising:
  - a plastic cone having a bottom aperture and first and second pairs of bilateral slits designed to receive the first and second pairs of prongs, the first and second pair of bilateral slits disposed orthogonally to each other;
  - a rubber overmold over the plastic cone; and
  - a sponge designed to fit over the rubber overmold.

10. The implement of claim 9, wherein the plastic cone has a recess designed to entrap the sponge between the plastic cone and the disk.

11. The implement of claim 9, wherein the rubber overmold is attached to the plastic cone.

12. The implement of claim 9, wherein each engagement member has a triangular cross section.

* * * * *